(12) United States Patent
Shekalim et al.

(10) Patent No.: US 9,586,029 B2
(45) Date of Patent: Mar. 7, 2017

(54) GUIDEWIRE HAVING SELECTIVELY ADJUSTABLE STIFFNESS AND TIP CURVATURE

(71) Applicant: CARDIOSERT LTD., Omer (IL)

(72) Inventors: Avraham Shekalim, Nesher (IL); Noam Peleg, Gan Ner (IL)

(73) Assignee: CARDIOSERT LTD., Omer (IL)

( * ) Notice: Subject to any disclaimer, the term of this patent is extended or adjusted under 35 U.S.C. 154(b) by 614 days.

(21) Appl. No.: 13/927,129

(22) Filed: Jun. 26, 2013

(65) Prior Publication Data

US 2014/0343457 A1    Nov. 20, 2014

Related U.S. Application Data

(60) Provisional application No. 61/825,119, filed on May 20, 2013.

(51) Int. Cl.
*A61B 5/00* (2006.01)
*A61M 25/00* (2006.01)
*A61M 25/09* (2006.01)

(52) U.S. Cl.
CPC ...... *A61M 25/09* (2013.01); *A61M 25/09025* (2013.01); *A61M 2025/0915* (2013.01);
(Continued)

(58) Field of Classification Search
CPC ........... A61M 2025/09116; A61M 2025/0915; A61M 2025/09175; A61M 25/09; A61M 25/09025; A61M 2025/09083; A61M 2025/0042; A61M 2025/0063; A61M 2025/09066; A61M 2025/09091; A61M 2025/091; A61M 2025/09125; A61M 2025/09133; A61M 2025/09166; A61M 25/09033; A61M 25/0147; A61M 25/0152; A61M 25/0045; A61M 25/0054;
(Continued)

(56) References Cited

U.S. PATENT DOCUMENTS

| 5,040,543 A | 8/1991 | Badera et al. |
| 5,605,162 A | 2/1997 | Mirzaee et al. |

(Continued)

FOREIGN PATENT DOCUMENTS

WO    2013118105    8/2013

*Primary Examiner* — Katherine M Shi
*Assistant Examiner* — Mohamed Gabr
(74) *Attorney, Agent, or Firm* — Mark M. Friedman

(57) ABSTRACT

A guidewire assembly having selectively adjustable stiffness and tip curvature includes a hollow guidewire having a distal portion terminating at a distal tip, a curvature-modifying element anchored to the distal tip, and a stiffness-modifying element displaceable within the hollow guidewire towards and away from the distal tip so as to vary a stiffness of the distal portion. The stiffness-modifying element and the curvature-modifying element are frictionally linked such that movement of the stiffness-modifying element from a current position over a first range of motion causes corresponding displacement of the curvature-modifying element, thereby modifying a state of curvature of at least part of the distal portion of the guidewire. Movement of the stiffness-modifying element beyond the first range of motion displaces the stiffness-modifying element relative to the curvature-modifying element.

11 Claims, 11 Drawing Sheets

(52) U.S. Cl.
CPC ............. *A61M 2025/09116* (2013.01); *A61M 2025/09175* (2013.01)

(58) Field of Classification Search
CPC .......... A61M 25/0138; A61M 25/0144; A61M 2025/09183; A51M 25/0136
USPC ........................................................ 600/585
See application file for complete search history.

(56) References Cited

U.S. PATENT DOCUMENTS

| | | |
|---|---|---|
| 5,944,689 A * | 8/1999 | Houser et al. ............. 604/95.04 |
| 7,481,778 B2 | 1/2009 | Cedro et al. |
| 7,491,224 B2 | 2/2009 | Cox et al. |
| 2002/0095102 A1 | 7/2002 | Winters |
| 2003/0088262 A1 | 5/2003 | Bonnette |
| 2005/0020998 A1* | 1/2005 | Bonnette et al. ............. 604/509 |
| 2007/0021685 A1 | 1/2007 | Oepen et al. |

* cited by examiner

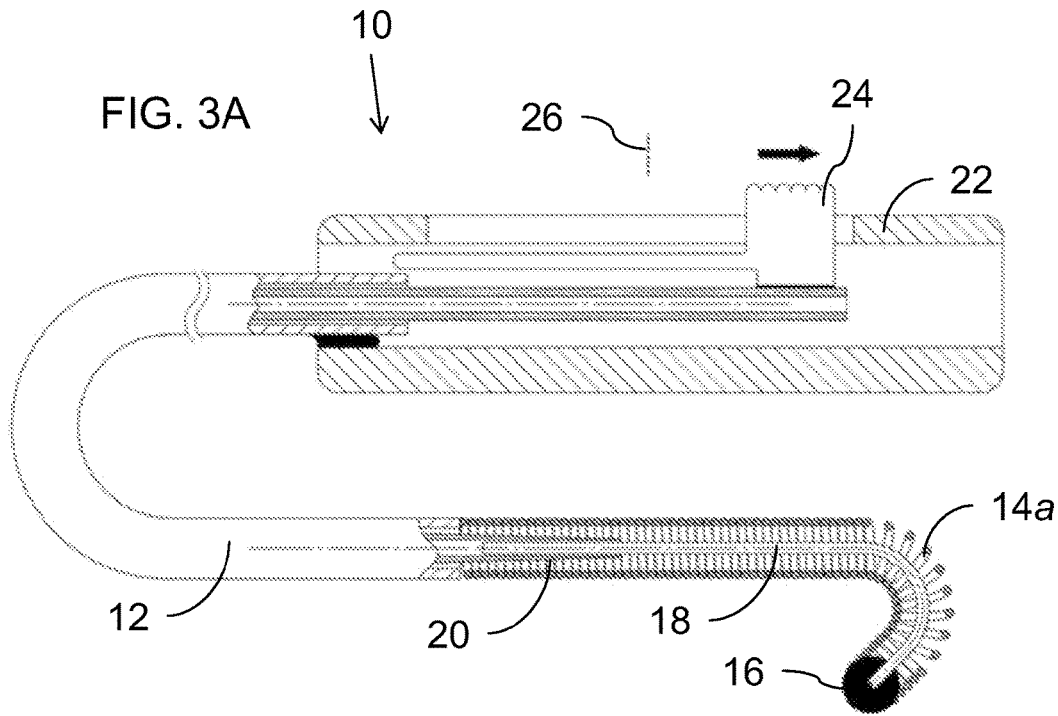
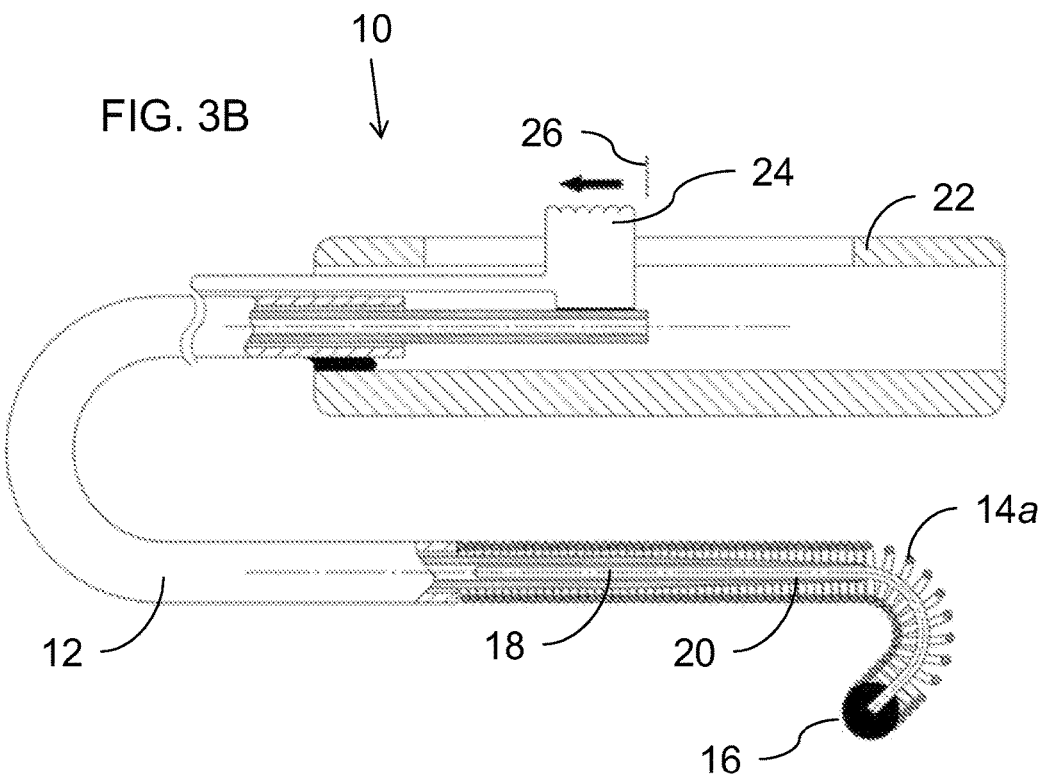

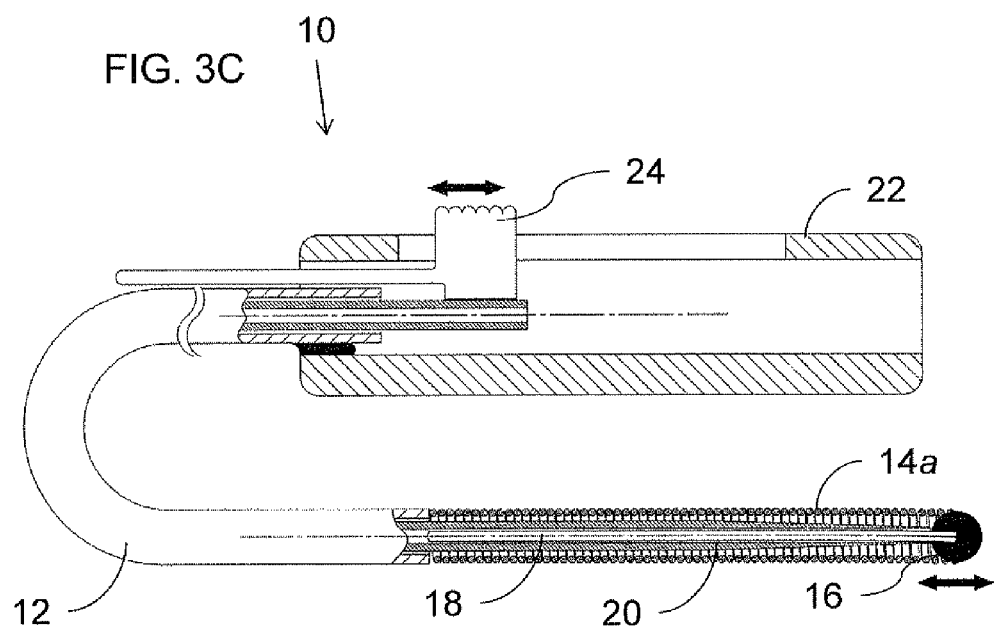
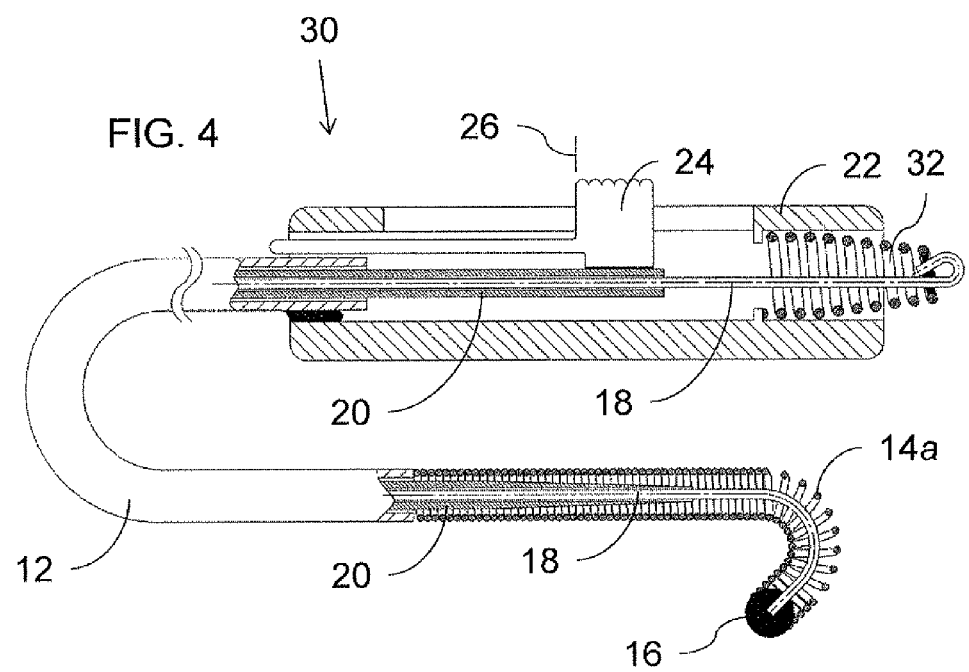

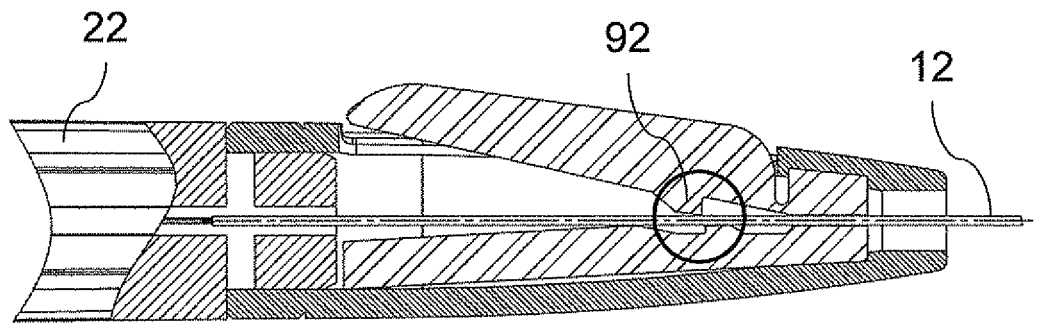
FIG. 12A
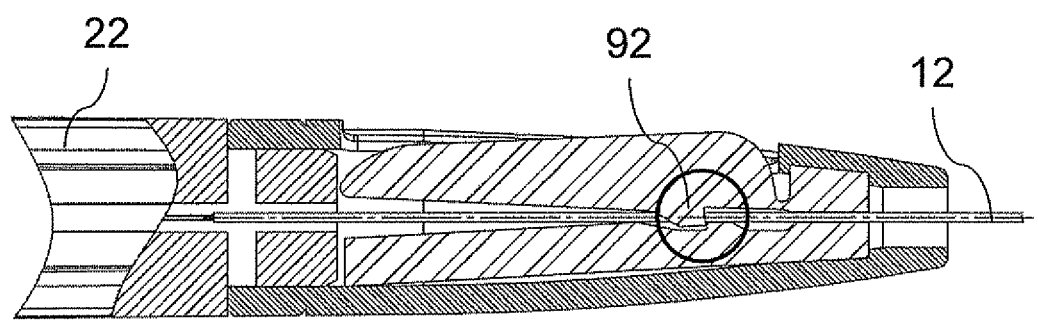
FIG. 12B
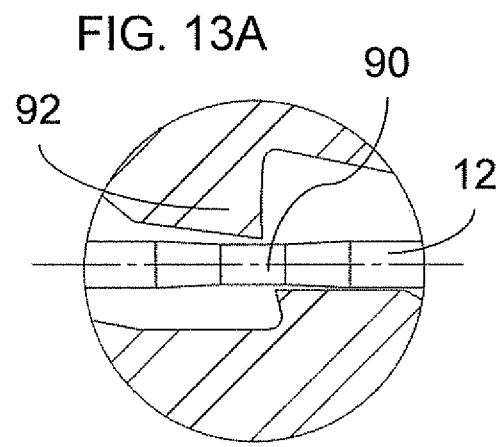 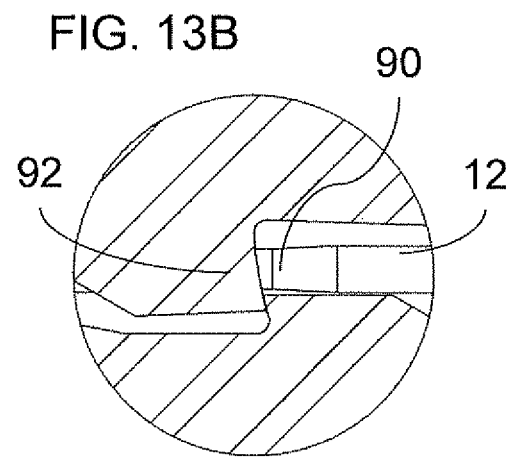
FIG. 13A     FIG. 13B

GUIDEWIRE HAVING SELECTIVELY ADJUSTABLE STIFFNESS AND TIP CURVATURE

FIELD AND BACKGROUND OF THE INVENTION

The present invention relates to medical devices for interventional cardiology and radiology.

Various procedures, such as percutaneous coronary intervention (PCI) procedures, involve navigating a guidewire along a convoluted intravascular access path and, in some cases, crossing a lesion or other obstacle with the guidewire. The different stages of guidewire deployment in such cases have differing requirements for guidewire tip curvature and guidewire stiffness.

Certain guidewires have capabilities for adjusting tip curvature. Others have capabilities for varying tip stiffness. However, existing adjustable guidewires typically only have the ability to vary one of these two parameters, or have a fixed correlation between them.

It would be advantageous to provide a guidewire in which the stiffness and tip curvature can be modified in an independent, or near-independent manner.

SUMMARY OF THE INVENTION

The present invention is a guidewire assembly having selectively adjustable stiffness and tip curvature, as well as systems and methods using such guidewire assemblies.

According to the teachings of the present invention there is provided, an apparatus comprising: (a) a hollow guidewire having a distal portion terminating at a distal tip; (b) a curvature-modifying element anchored to the distal tip and extending proximally from the distal tip through at least the distal portion of the guidewire, the distal portion and the curvature-modifying element being configured such that axial displacement of the curvature-modifying element within a first range of motion modifies a state of curvature of at least part of the distal portion of the guidewire; and (c) a stiffness-modifying element displaceable within the hollow guidewire towards and away from the distal tip so as to vary a degree of overlap between the stiffness-modifying element and the distal portion, thereby varying a stiffness of the distal portion, wherein the stiffness-modifying element and the curvature-modifying element are frictionally linked such that: (i) movement of the stiffness-modifying element from a current position over a first range of motion causes corresponding displacement of the curvature-modifying element, thereby modifying a state of curvature of at least part of the distal portion of the guidewire; and (ii) movement of the stiffness-modifying element beyond the first range of motion displaces the stiffness-modifying element relative to the curvature-modifying element.

According to a further feature of an embodiment of the present invention, at least part of the distal portion is formed as a helical spring biased to assume a deflected form, and wherein retraction of the curvature-modifying element is effective to straighten the at least part of the distal portion.

According to a further feature of an embodiment of the present invention, the curvature-modifying element comprises a wire, and wherein the stiffness-modifying element comprises a sleeve at least partially circumscribing the wire.

According to a further feature of an embodiment of the present invention, a proximal end of the hollow guidewire is connected to a handle, and wherein the sleeve extends along the hollow guidewire to an adjustment mechanism associated with the handle, the sleeve being mechanically linked to the adjustment mechanism for being advanced and retracted relative to the guidewire.

According to a further feature of an embodiment of the present invention, the wire extends within the sleeve along a length of the guidewire and is anchored to the handle via a resilient element.

According to a further feature of an embodiment of the present invention, a proximal end of the wire is attached to a second adjustment mechanism configured for generating displacements of the wire relative to the guidewire.

According to a further feature of an embodiment of the present invention, a proximal end of the hollow guidewire is connected to a handle, and wherein the stiffness-modifying element extends along the hollow guidewire to an adjustment mechanism associated with the handle, the stiffness-modifying element being mechanically linked to the adjustment mechanism for being advanced and retracted relative to the guidewire.

According to a further feature of an embodiment of the present invention, the handle comprises an integrated cutter element selectively deployable to sever the guidewire and the stiffness-modifying element from the handle. According to a further feature of an embodiment of the present invention, a majority of the hollow guidewire has a first external diameter, and wherein a region of the hollow guidewire located adjacent to the integrated cutter element has a second diameter smaller than the first diameter.

According to a further feature of an embodiment of the present invention, a majority of the hollow guidewire has a first external diameter, and wherein a proximal region of the hollow guidewire includes a severance region having a second diameter smaller than the first diameter, the severance region extending for not more than one percent of a length of the hollow guidewire.

According to a further feature of an embodiment of the present invention, the hollow guidewire has a length and an external diameter, the length being in excess of 1000 times the external diameter.

According to a further feature of an embodiment of the present invention, the hollow guidewire is configured for use in a percutaneous coronary intervention.

BRIEF DESCRIPTION OF THE DRAWINGS

The invention is herein described, by way of example only, with reference to the accompanying drawings, wherein:

FIGS. 3A-3C are views similar to FIG. 1 showing a withdrawn, advanced and fully advanced position, respectively, of the stiffening element;

FIG. 4 is a schematic cross-sectional view illustrating a variant of the embodiment of FIG. 1;

FIGS. 12A and 12B are enlarged longitudinal-cross-sectional views taken through the cutters of FIGS. 11A and 11B, respectively; and FIGS. 13A and 13B are enlarged views of the encircled regions of FIGS. 12A and 12B, respectively.

DESCRIPTION OF THE PREFERRED EMBODIMENTS

The present invention is a guidewire assembly having selectively adjustable stiffness and tip curvature, as well as systems and methods using such guidewire assemblies.

The principles and operation of guidewire assemblies according to the present invention may be better understood with reference to the drawings and the accompanying description.

Figure 1:
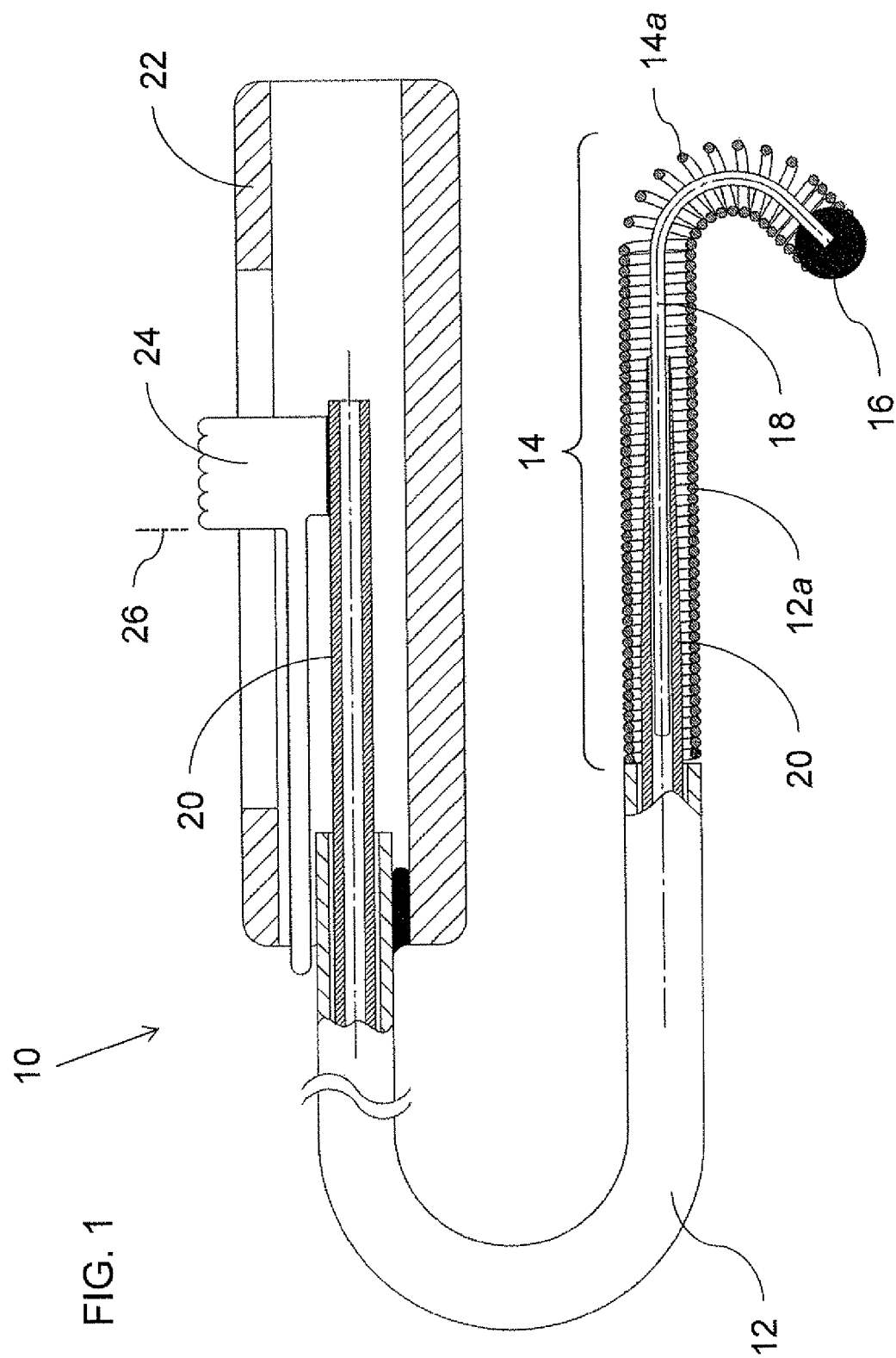
FIG. 1 is a schematic cross-sectional view through a guidewire assembly, constructed and operative according to an embodiment of the present invention, illustrating a stiffening element in an intermediate position and a distal tip in a fully deflected position.

Referring now to the drawings, FIG. 1-3C illustrate a first embodiment of an apparatus, particularly a guidewire assembly, generally designated 10, constructed and operative according to an embodiment of the present invention. In general terms, apparatus 10 includes a hollow guidewire 12 having a distal portion 14 terminating at a distal tip 16. Within hollow guidewire 12 is deployed a curvature-modifying element 18 anchored to distal tip 16 and extending proximally from the distal tip through at least distal portion 14 of guidewire 12. Distal portion 14 and curvature-modifying element 18 are configured such that axial displacement of curvature-modifying element 18 within a first range of motion modifies a state of curvature of at least a part 14a of the distal portion of guidewire 12, for example, as illustrated in the sequence of FIGS. 1, 2A and 2B.

Apparatus 10 also includes a stiffness-modifying element 20, displaceable within hollow guidewire 12 towards and away from distal tip 16 so as to vary a degree of overlap between the stiffness-modifying element and the distal portion, thereby varying a stiffness of the distal portion.

According to certain particularly preferred embodiments of the present invention, stiffness-modifying element 20 and curvature-modifying element 18 are frictionally linked such that movement of stiffness-modifying element 20 from a current position over a first range of motion causes corresponding displacement of curvature-modifying element 18, thereby modifying a state of curvature of at least part of the distal portion of the guidewire. The structure is configured so that movement of stiffness-modifying element 20 beyond the first range of motion overcomes the static frictional engagement so as to displace stiffness-modifying element 20 relative to curvature-modifying element 18. This defines a new position of stiffness-modifying element 20 and corresponding degree of overlap within distal portion 14, while at the same time allowing control of curvature-modifying element 18 to increase and decrease deflection of distal tip 16 via newly positioned frictional engagement between stiffness-modifying element 20 and curvature-modifying element 18.

At this stage, it will already be apparent that the present invention provides highly advantageous features. Specifically, the design parameters of a guidewire, often with a diameter of less than 0.5 millimeter and a length in excess of 1 meter, render it challenging to implement independent control of displaceable control elements for controlling both curvature and stiffness at the distal tip of the guidewire. According to the teachings of certain embodiments of the present invention, friction between the two control elements is actually used to advantage and, in some cases, allows selective control of two distinct adjustable parameters my moving a single control element. This and other advantages of the present invention will be better understood by reference to the following description.

Referring now to the features of apparatus 10 in more detail, the invention relates primarily, although not exclusively, to guidewires for navigation, typically under real time imaging, to an intrabody site, and which then serve to guide one or more tool or implant to that site. The invention is believed to be of particular value in the context of intravascular procedures, and especially percutaneous coronary intervention (PCI) procedures. Guidewires for such applications typically have a length-to-diameter ratio in excess of 1000. Typical diameters are less than 1 millimeter, including guidewires of gauge 0.035 and 0.038 inch, and the invention exhibits particular advantages for smaller gauge guidewires of diameter less than 0.5 mm, such as 0.014 inch gauge common in PCI procedures, and 0.009 inch gauge which may be used for a part or the entirety of a guidewire, for example, for brain surgery.

Typical lengths of guidewire 12 are in excess of 1 meter, and most preferably in the range of 1.5-2 meters. It will be noted that the schematic cross-sectional views used to illustrate features of the present invention for the purpose of this patent application are shown not to scale, and omit the majority of the length of the guidewire, in order to facilitate an understanding of the principles of the invention.

At least distal portion 14 of hollow guidewire 12 is preferably implemented as a helical spring 12a, thereby providing a highly conformable and non-penetrating tip for safely navigating within the body with minimum risk of perforation. Typically, the remaining length of hollow guidewire 12 is implemented using a solid tube of biocompatible material with suitable properties, as is known in the art. A typical example is a cylindrical structure formed of stainless steel. It should be noted however that hollow guidewire 12 according to the present invention is supplemented by at least one, and in some cases two, additional elements extending along most of its length, and that all of these elements contribute to the mechanical properties of the guidewire assembly. As a result, in certain cases, the main length of hollow guidewire 12 may be formed from polymer materials, with the majority of the required mechanical strength provided by inner sleeve 20. Conversely, hollow guidewire 12 may be formed as a metal tube while the inner sleeve is implemented as a polymer element. A range of further variants and combinations of structures and materials effective to provide the required combination of mechanical properties will be clear to a person ordinarily skilled in the art on the basis of this description.

Figure 2A:
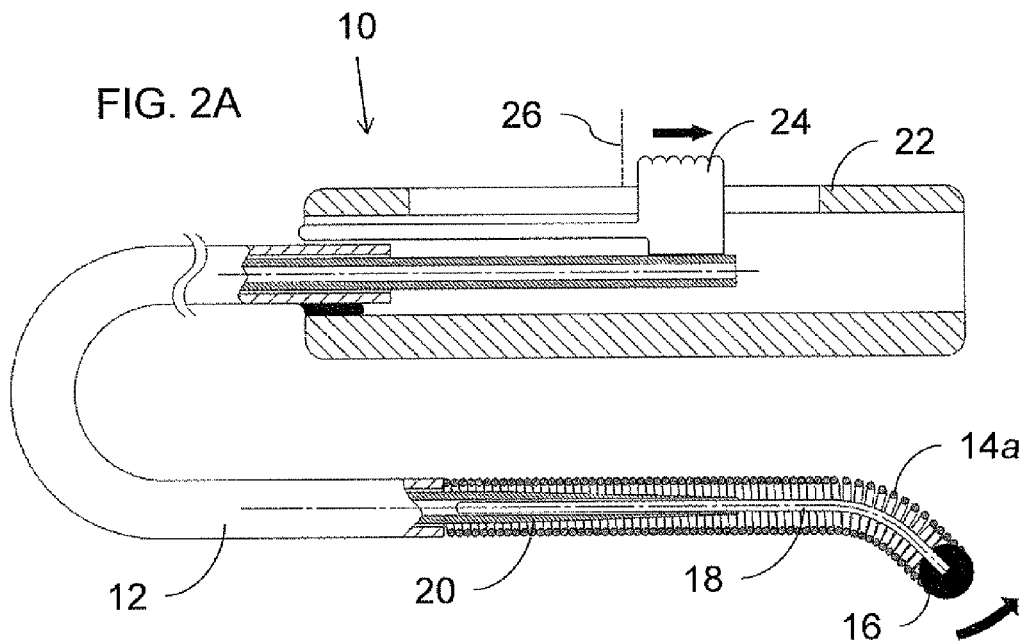
FIGS. 2A and 2B are views similar to FIG. 1 showing two stages of straightening the deflection of the distal tip.
Figure 2B:
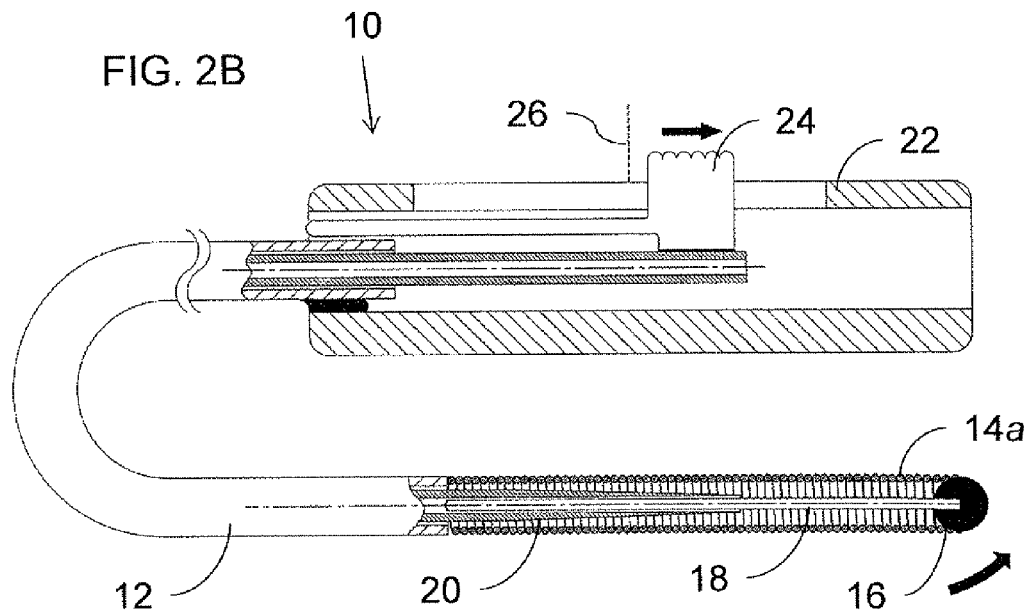

At least a part 14a of distal portion 14 is configured to exhibit controllable deflection between a deflected form (FIG. 1) and a partially or fully straightened form (FIGS. 2A and 2B). The "deflected" form may include a localized bend, or may be a curve extending along a length of the guidewire at or near the tip. In the preferred example illustrated here, The helical spring 12a and/or curvature-modifying element 18 are biased to assume the deflected form, and retraction of the curvature-modifying element 18 is effective to straighten part 14a of the distal portion. Specifically, helical spring 12a within part 14a is biased to a state as shown in which successive coils on the inside of the deflected form are closed together while the coils on the outside of the deflected form are spaced apart. Tension applied to curvature-modifying element 18 thus tends to close together the coils on the open side of the deflected form, thereby straightening it.

It should be noted that alternative configurations, such as where the distal portion of the guidewire is biased to return to a straight state and tension applied to an asymmetric actuator wire generates lateral deflection, also fall within the scope of the present invention.

The curvature-modifying element is preferably implemented as a wire 18, which is shown here as a central wire axially positioned within hollow guidewire 12. In the embodiment of FIG. 1, wire 18 extends from distal tip 16 along only part of the length of guidewire 12. The stiffness-modifying element is preferably implemented as a sleeve 20 at least partially circumscribing wire 18. Sleeve 20 is most preferably a tube fully circumscribing wire 18 over their length of overlap.

A proximal end of hollow guidewire 12 is preferably connected to a handle 22 which provides manual control over movement of the guidewire during insertion. Handle 22 is linked to guidewire 12 so as to allow application of axial (longitudinal) force to advance and withdraw the guidewire, as well as torque for orienting the direction of tip deflection within the body during navigation. Sleeve 20 preferably extends along hollow guidewire 12 to an adjustment mechanism 24 associated with handle 22. In a preferred case illustrated here, adjustment mechanism 24 includes a manually operable slider mechanically linked to sleeve 20 for advancing and retracting sleeve 20 relative to guidewire 12.

Operation of apparatus 10 is as follows. By harnessing static friction between the sleeve 20 and wire 18, a single adjustment mechanism, slider 24, is used to achieve two independent types of control over the properties of the guidewire tip. Specifically, referring to an initial position of slider 24 denoted by dashed line 26 of FIG. 1, a slight movement of sleeve 20 proximally, i.e., away from the distal, tip, increases the tension in wire 18 at the distal tip due to friction between the sleeve and the wire. As a result the spaces between the turns of the coil spring on the outside of the bent portion are gradually closed together, thereby progressively reducing its curve (FIG. 2A) until it is ultimately straightened (FIG. 2B). As mentioned, the coils on the inside of the bent portion are already closed together in the relaxed curved state.

Conversely, a slight movement of sleeve 20 distally, i.e., towards the distal tip, decreases tension of the central wire at the distal tip due to the static frictional engagement between sleeve 20 and wire 18. As a result, the spaces between the turns of the coil spring on the outside of the curved portion expand back to their relaxed state and the tip returns to its initial preset curved form.

The second type of adjustment occurs when a larger displacement of the displaceable sleeve 20 is initiated, thereby applying enough force, resisted by the anchoring of wire 18 at distal tip 16 and the properties of helical spring 12a, to overcome the friction between the displaceable tube and the central wire. In this case, the inner displaceable sleeve assumes a new position, either retracted away from the distal tip of the guidewire as shown in FIG. 3A to make the tip portion more flexible or "floppy", or advanced towards the distal tip as shown in FIG. 3B, making the tip portion stiffer. After the sleeve 20 assumes its new position, static frictional engagement between sleeve 20 and wire 18 again allows the same adjustment of the curvature of the tip described above by subsequent small movement of the sleeve.

When sleeve 20 is further advanced, as illustrated in FIG. 3C, sleeve 20 preferably extends to engage distal tip 16, typically inducing a relatively straight state of the tip portion. In this state, further force applied to slider 24 to advance sleeve 20 directly displaces distal tip 16 linearly, allowing the operator to deliver manual impacts to a lesion or other obstruction that must be crossed.

Whenever the static friction between the inner sleeve and the central wire is overcome, the sleeve can smoothly run over the central wire. Moving the inner sleeve forward to a position where its distal end is next to the tip increases the stiffness (tip load) of the guidewire while moving it backward to a position away from the tip reduces the stiffness such that the guidewire becomes less stiff, i.e., more pliant or "floppy".

At any position of the inner sleeve in which the end of the sleeve falls short of the distal tip, the curved portion can be manipulated (partially or fully straightened, or returned to its curved state) by slight backward and forward movement of the inner sleeve.

The range of stiffnesses which can be achieved by the adjustment of the present invention preferably spans the normal range of stiffnesses as measured by standard techniques such as the "tip load test" which measures the axial force required to generate buckling of the last 10 millimeters of the guidewire while the rest of the guidewire is supported. The guidewires of the present invention preferably span the majority of a range of 0.3-30 grams force, and most preferably, the entirety of that range.

Turning now briefly to FIG. 4, this illustrates a variant of apparatus 10, designated as apparatus 30, in which equivalent elements are labeled similarly. Apparatus 30 differs from apparatus 10 in that wire 18 here extends within sleeve 20 along the length of guidewire 12 and is anchored to handle 22 via a resilient element illustrated here as spring 32. The function of spring 32 is to maintain slight tension in wire 18 so that it does not become slack during retraction of slider 24. Otherwise, apparatus 30 is structurally and functionally equivalent to apparatus 10, and all of the above description should be considered as applicable to apparatus 30.

Figure 5:
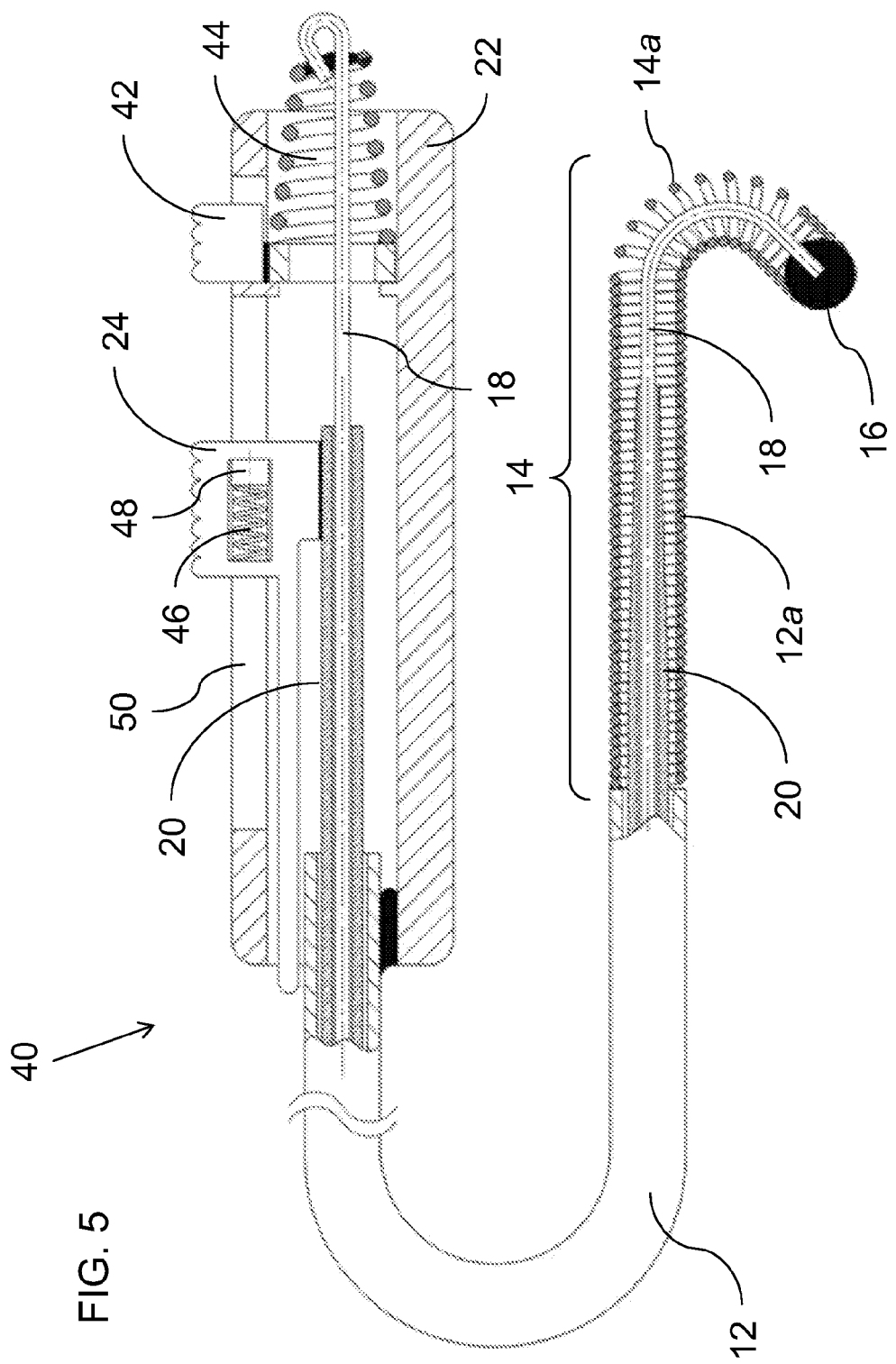
FIG. 5 is a schematic cross-sectional view through a guidewire assembly, constructed and operative according to a further variant of the embodiment of FIG. 1 employing separate controls for control of stiffness and curvature.

Turning now to FIG. 5, this shows a variant of apparatus 30, designated as apparatus 40, in which equivalent elements are labeled similarly. In certain cases, it may be advantageous to provide separate adjustment mechanisms associated with handle 22 for controlling the respective adjustments of tip deflection and stiffness. To this end, in addition to slider 24 that controls motion of sleeve 20, apparatus 40 also includes a second slider (adjustment mechanism) 42 configured for generating displacements of wire 18 relative to the guidewire. In the preferred implementation as illustrated here, the principles of operation of adjustment of tip stiffness and deflection remain exactly as in apparatus 10 and 30 described above, with small movements of wire 18 occurring while static frictional engagement is maintained between sleeve 20 and wire 18, and larger movements of sleeve 20 being implemented by overcoming that static frictional engagement. The distinctive features of apparatus 40 therefore relate to the implementation of the control mechanism in handle 22, which will now be described.

As mentioned, second slider 42 is deployed for generating displacements of wire 18. Motion of slider 42 is here illustrated as applying tension to wire 18 via a spring 44. The applied tension results in small movements of wire 18 together with sleeve 20, resulting in controlled straightening of tip portion 14a, as described above with reference to FIGS. 2A and 2B. Larger movements of sleeve 20 overcoming the frictional locking between sleeve 20 and wire 18 are achieved by displacing the first slider 24.

A further feature illustrated in the context of apparatus 40 is a curvature-reset mechanism which ensures that the deflection of the guidewire tip returns to its default deflected state after each adjustment of the position of sleeve 20. Specifically, slider 24 is here mounted on a rail 50 via a sliding friction mount 48 which engages a slot in slider 24. A slider spring 46 biases slider 24 against sliding friction mount 48 so that the friction mount assumes a rest position at one end of the slot, as shown.

To achieve a forward (distal) movement of sleeve 20, slider 24 is manually advanced, directly pushing friction mount 48 along rail 50 to a new position. During a retraction (proximal) movement of slider 24, slider spring 46 is compressed at the beginning of the motion before friction mount 48 is displaced. Then when slider 24 is released, it returns through a correspond small movement in the forward (distal) direction as slider spring 46 is released. This serves to return the distal part 14a of guidewire 12 to its deflected state after it was momentarily straightened during the retraction of sleeve 20.

Figure 6:
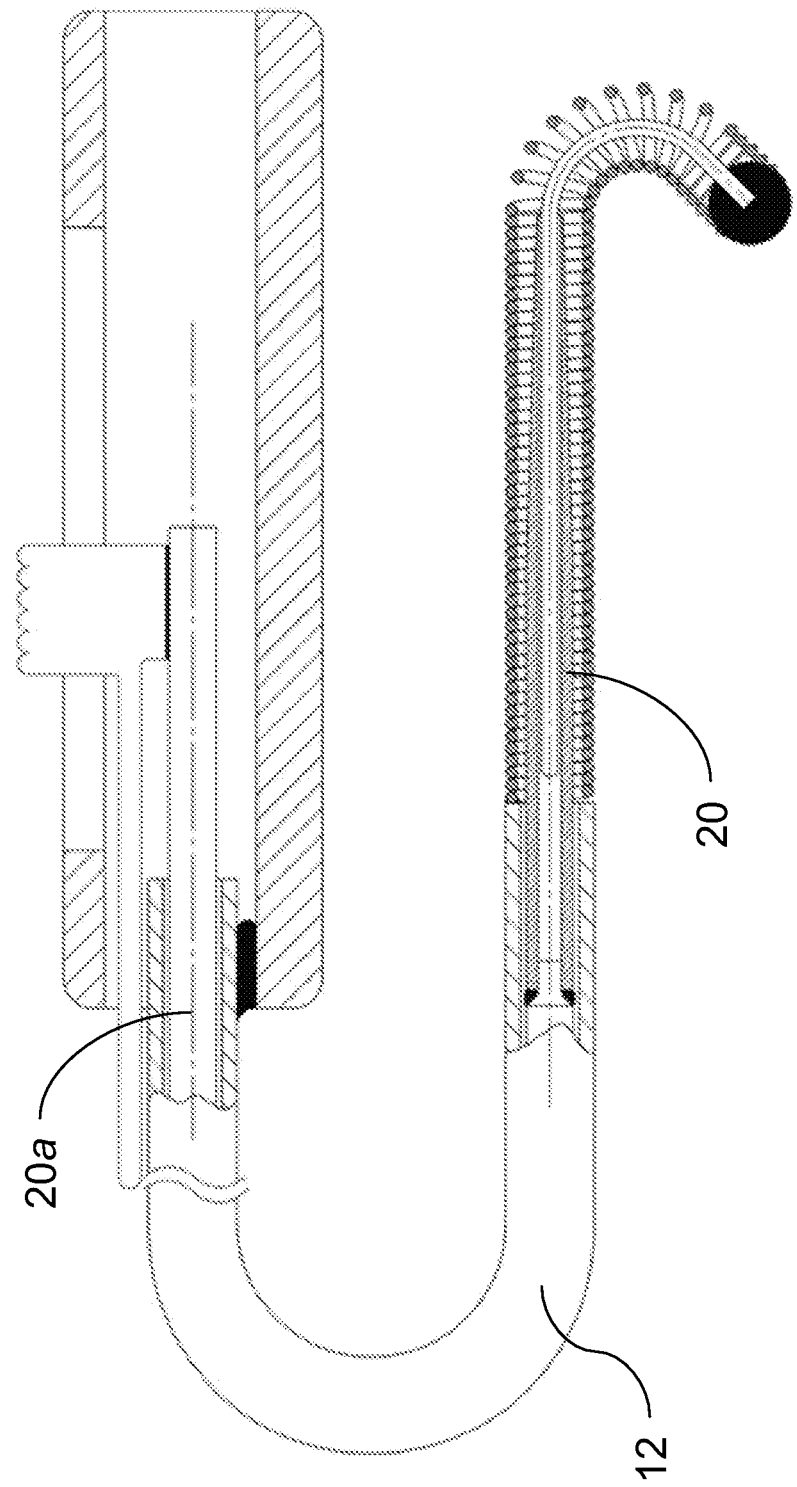
FIG. 6 is a schematic cross-sectional view through a guidewire assembly, constructed and operative according to a further variant of the embodiment of FIG. 1.
Figure 7:
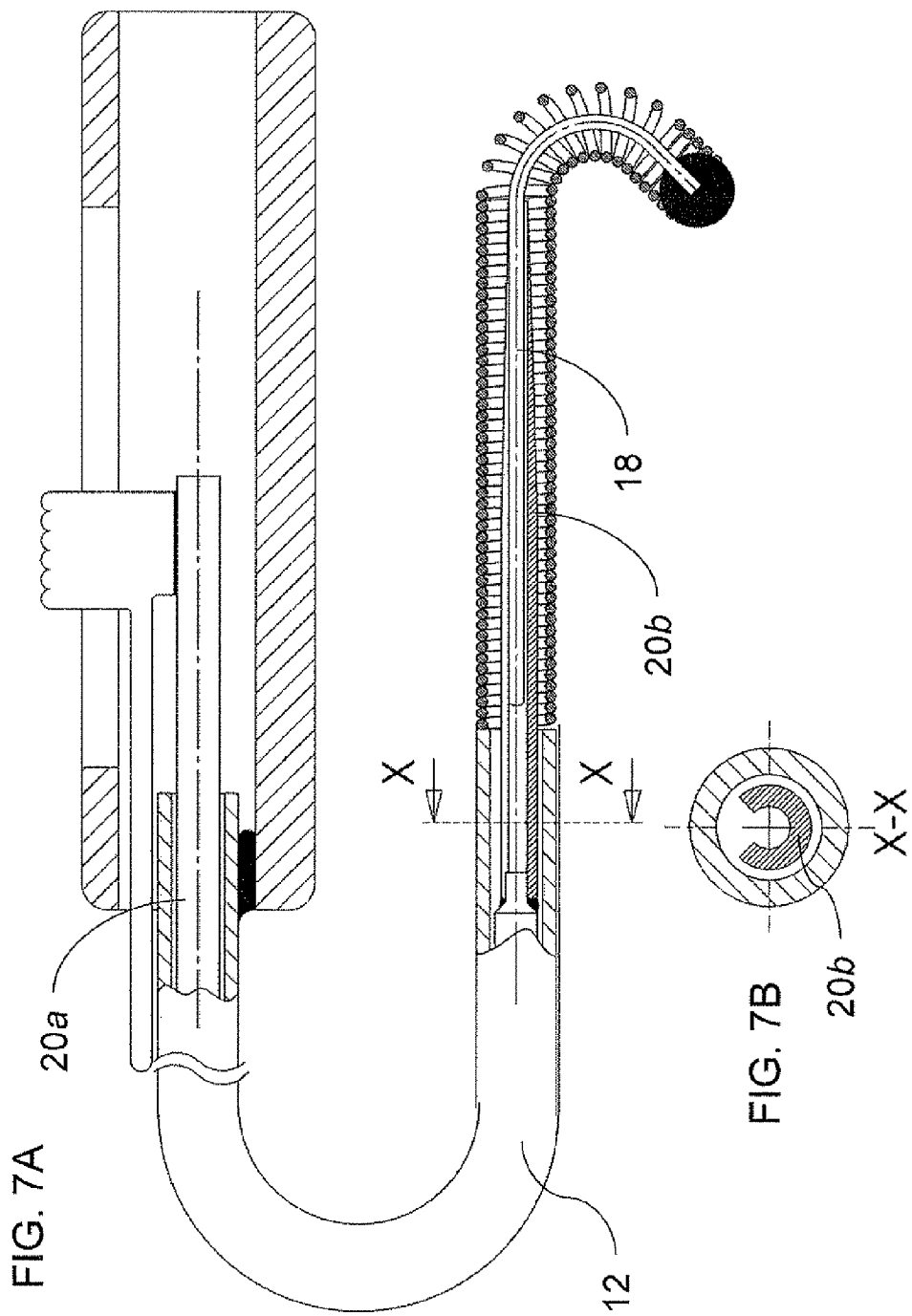
FIG. 7A is a schematic cross-sectional view through a guidewire assembly, constructed and operative according to a further variant of the embodiment of FIG. 1.
FIG. 7B is a schematic cross-sectional view taken along line X-X of FIG. 7A.
Figure 8:
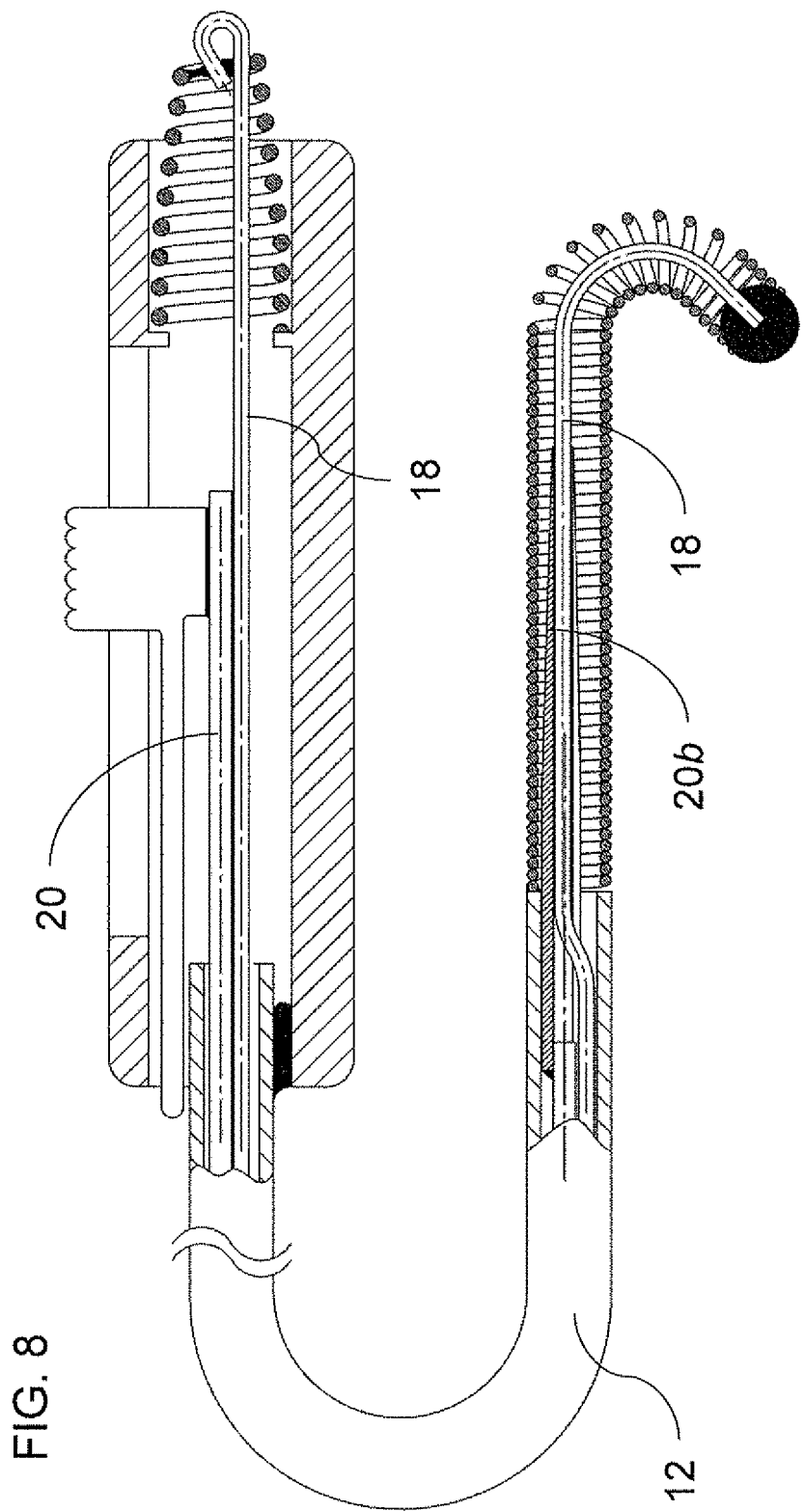
FIG. 8 is a schematic cross-sectional view through a guidewire assembly, constructed and operative according to a further variant of the embodiment of FIG. 1.

Turning now to FIGS. 6-8, it should be noted that the specific structure of the sleeve illustrated thus far for stiffness-modifying element 20 is one preferred example, but that many variant embodiments may be implemented within the scope of the invention. For example, FIG. 6 illustrates an alternative embodiment in which stiffness-modifying element 20 is implemented as a tube or sleeve within a distal region of hollow guidewire 12, while its major part extending along most of the length of the guidewire to the handle is implemented as a solid actuator shaft 20a. The structure and operation of this structure is otherwise identical to that of FIG. 1 as described above.

Turning now to FIG. 7A, this shows a structure similar to FIG. 6 except that the distal region of stiffness-modifying element 20 is implemented as an open-sided sleeve or tube 20b, as best seen in the cross-sectional view of FIG. 7B. The resulting partial encircling of wire 18 is still sufficient to achieve the required frictional engagement for operation of the invention in the same manner as described above.

Turning now to FIG. 8, this shows a further variant implementation similar to apparatus 30 described above, in which stiffness-modifying element 20 and curvature-modifying element 18 are formed as parallel actuator elements running along most of the length of hollow guidewire 12, and assume a form designed to provide the recited frictional engagement just in the distal region of hollow guidewire 12. In the case illustrate here, the cross-section of the engagement is again an open-sided tube. In all other respects, the structure and operation of this implementation is equivalent to that described above with reference to apparatus 10 and 30.

Figure 9:
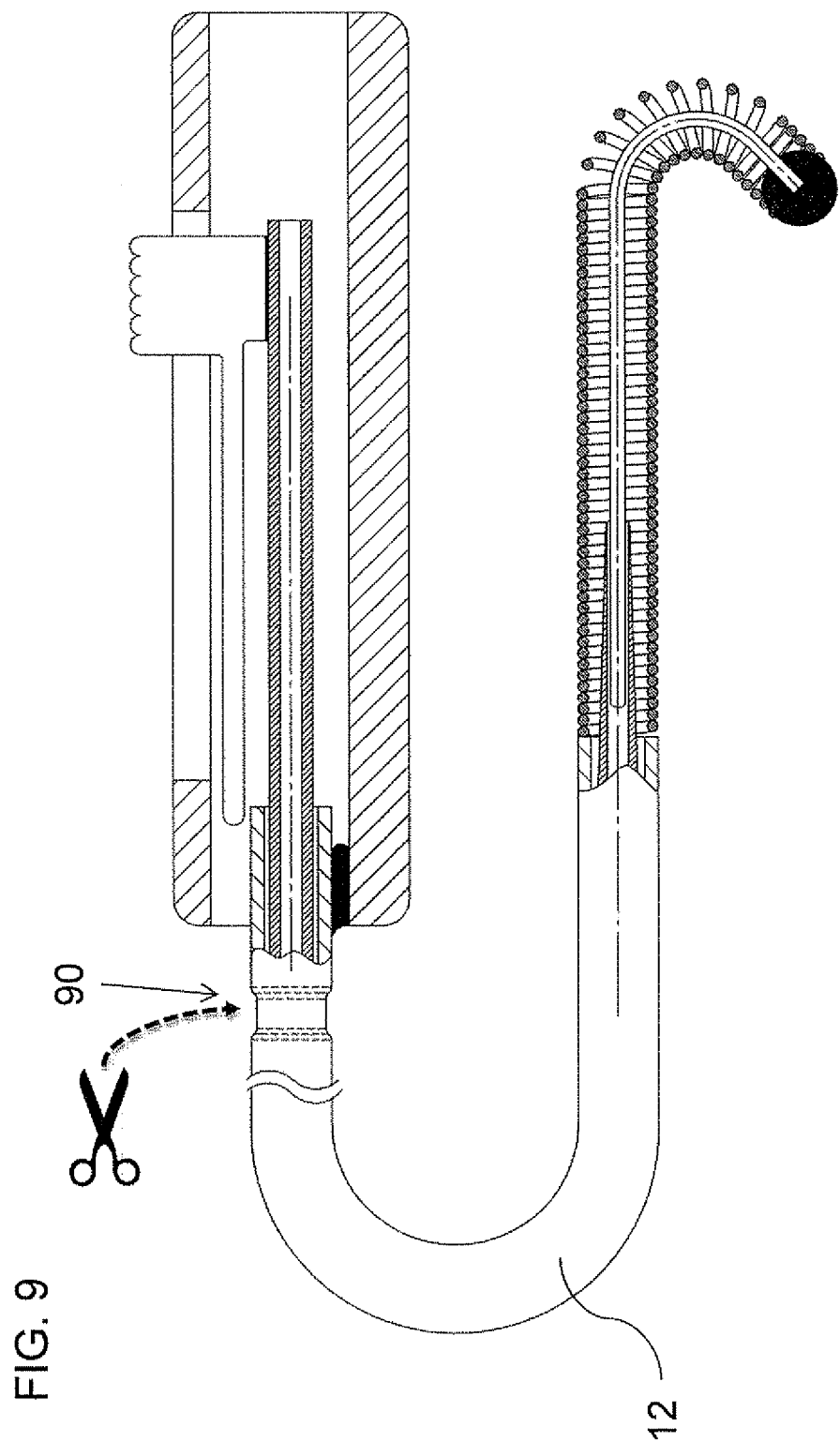
FIG. 9 is a schematic cross-sectional view illustrating a modification, applicable to all of the above-illustrated implementations of a guidewire assembly, showing a reduced-diameter region for severing the guidewire to provide a non-damaging end for subsequent threading of devices along the guidewire.
Figure 10:
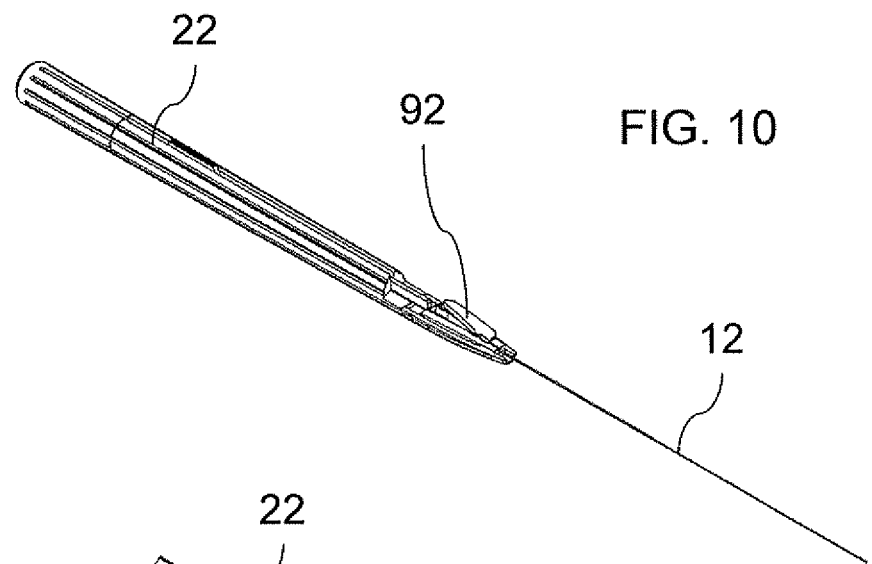
FIG. 10 is an isometric view illustrating a tip portion or a guidewire operating handle with an integrated cutter, constructed and operative according to an embodiment of the present invention.
Figure 11A:
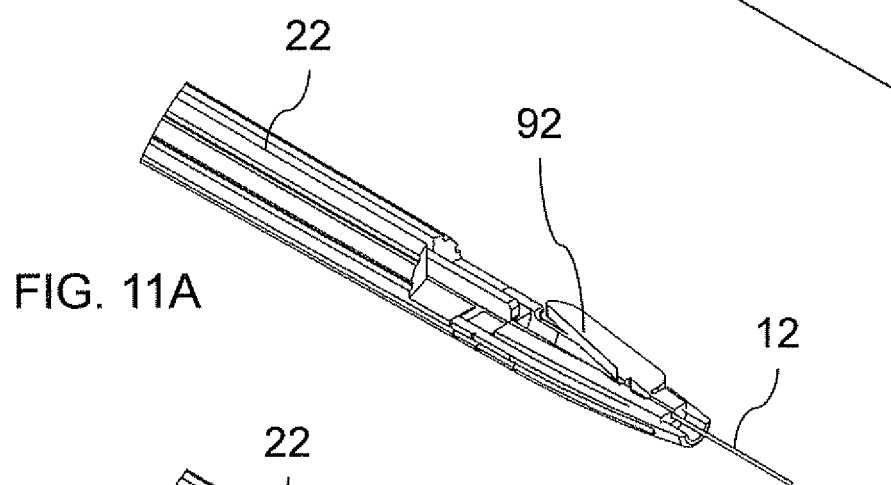
FIGS. 11A and 11B are enlarged views of the cutter of FIG. 10 before and after actuation, respectively.
Figure 11B:
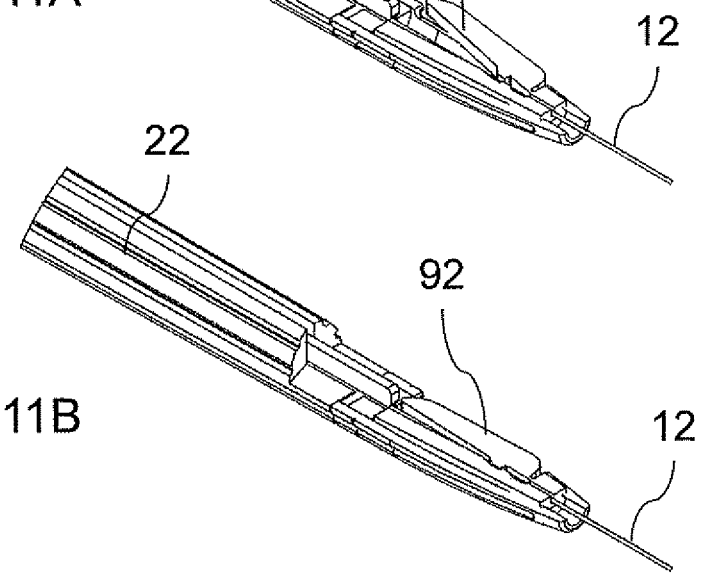

Turning now to FIG. 9, this illustrates schematically a further optional feature which may be used to advantage with any of the embodiments of the present invention described herein. Specifically, in order to simplify use of the guidewires of the present invention after deployment, it is sometimes preferred to cut the guidewire close to the handle so that there is a free end of the guidewire available onto which a tool or implant can be threaded for deployment within the body. However, it has been found that cutting of the guidewire often results in a sharp or abrasive cut end which may project outwards beyond the overall profile of the guidewire, and may cause damage to devices subsequently threaded over the cut end.

As a solution to this problem, one aspect of the present invention provides a proximal region of the hollow guidewire includes a severance region 90 having a diameter smaller than the predominant external diameter of the guidewire, the severance region extending for not more than one percent of a length of the hollow guidewire. As a result of the reduced diameter, even if cutting of the guidewire results in a sharp or abrasive projection outside the local diameter of the guidewire, the sharp or abrasive features lie within the overall cylindrical inner diameter of a device subsequently threaded onto the guidewire, and are therefore not damaged by the sharp features. The use of a short severance region also ensures that the larger diameter part of the guidewire quickly aligns itself within the channel of any device subsequently threaded thereon, further helping to ensure that any sharp features remaining from the cutting of the guidewire do not damage the device.

Turning now to FIGS. 10-13B, to implement cutting of the guidewire after positioning, and a corresponding method of the present invention, the various handle designs described above, or any other guidewire-positioning handle, may advantageously include an integrated cutter element 92 selectively deployable to sever guidewire 12 and all contained elements (e.g., stiffness-modifying element 20) from the handle. FIGS. 11A and 12A show an enlarged isometric and cross-sectional view, respectively, of the integrated cutter element prior to actuation of the cutter, while FIGS. 11B and 12B show similar views after actuation of the cutter.

Most advantageously, the cutter configuration of FIGS. 12A and 12B is implemented in combination with the reduced diameter severance region 92 positioned adjacent to the integrated cutter element, as illustrated in the enlarged views of FIGS. 13A and 13B.

To the extent that the appended claims are drafted without multiple dependencies, this is been done to comply with procedural requirements or preferences in the jurisdiction of first filing. All combinations of claimed features that could be introduced by use of multiple dependencies are hereby explicitly included in the scope of the disclosure unless inherently incompatible or explicitly disclaimed.

It will be appreciated that the above descriptions are intended only to serve as examples, and that many other embodiments are possible within the scope of the present invention as defined in the appended claims.

What is claimed is:
1. An apparatus comprising:
(a) a hollow guidewire having a distal portion terminating at a distal tip, at least part of said distal portion being formed as a helical spring biased to assume a deflected form;

(b) a curvature-modifying element anchored to said distal tip and extending proximally from said distal tip through at least said distal portion of said guidewire, said distal portion and said curvature-modifying element being configured such that axial displacement of said curvature-modifying element within a first range of motion modifies a state of curvature of said at least part of said distal portion of the guidewire, refraction of said curvature-modifying element being effective to straighten said at least part of said distal portion by closing together successive coils of said helical spring; and (c) a stiffness-modifying element displaceable within said hollow guidewire towards and away from said distal tip so as to vary a degree of overlap between said stiffness-modifying element and said distal portion, thereby varying a stiffness of said distal portion, wherein said stiffness-modifying element and said curvature-modifying element are frictionally linked such that:

(i) movement of said stiffness-modifying element from a current position over a first range of motion causes corresponding displacement of said curvature-modifying element, thereby modifying a state of curvature of at least part of said distal portion of the guidewire, said stiffness-modifying element and said curvature-modifying element being configured to create therebetween sufficient frictional engagement that retraction of said stiffness-modifying element applies sufficient frictional force to said curvature-modifying element to fully straighten said at least part of said distal portion; and (ii) movement of said stiffness-modifying element beyond said first range of motion overcomes said frictional engagement so as to displace said stiffness-modifying element relative to said curvature-modifying element.

2. The apparatus of claim 1, wherein said curvature-modifying element comprises a wire, and wherein said stiffness-modifying element comprises a sleeve at least partially circumscribing said wire.

3. The apparatus of claim 2, wherein a proximal end of said hollow guidewire is connected to a handle, and wherein said sleeve extends along said hollow guidewire to an adjustment mechanism associated with said handle, said sleeve being mechanically linked to said adjustment mechanism for being advanced and retracted relative to said guidewire.

4. The apparatus of claim 3, wherein said wire extends within said sleeve along a length of said guidewire and is anchored to said handle via a resilient element.

5. The apparatus of claim 3, wherein a proximal end of said wire is attached to a second adjustment mechanism configured for generating displacements of said wire relative to said guidewire.

6. The apparatus of claim 1, wherein a proximal end of said hollow guidewire is connected to a handle, and wherein said stiffness-modifying element extends along said hollow guidewire to an adjustment mechanism associated with said handle, said stiffness-modifying element being mechanically linked to said adjustment mechanism for being advanced and retracted relative to said guidewire.

7. The apparatus of claim 6, wherein said handle comprises an integrated cutter element selectively deployable to sever said guidewire and said stiffness-modifying element from said handle.

8. The apparatus of claim 7, wherein a majority of said hollow guidewire has a first external diameter, and wherein a region of said hollow guidewire located adjacent to said integrated cutter element has a second diameter smaller than said first diameter.

9. The apparatus of claim 1, wherein a majority of said hollow guidewire has a first external diameter, and wherein a proximal region of said hollow guidewire includes a severance region having a second diameter smaller than said first diameter, said severance region extending for not more than one percent of a length of said hollow guidewire.

10. The apparatus of claim 1, wherein said hollow guidewire has a length and an external diameter, said length being in excess of 1000 times said external diameter.

11. The apparatus of claim 1, wherein said hollow guidewire is configured for use in a percutaneous coronary intervention.

* * * * *